US008918164B2

(12) United States Patent
Adler et al.

(10) Patent No.: US 8,918,164 B2
(45) Date of Patent: *Dec. 23, 2014

(54) METHOD AND SYSTEM FOR DETECTING COLORIMETRIC ABNORMALITIES IN VIVO

(71) Applicant: Given Imaging Ltd., Yoqneam (IL)

(72) Inventors: Doron Adler, Nesher (IL); Ofra Zinaty, Haifa (IL); Daphna Levy, Carmiel (IL); Arkady Glukhovsky, Santa Clarita, CA (US)

(73) Assignee: Given Imaging Ltd., Yoqneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/046,258

(22) Filed: Oct. 4, 2013

(65) Prior Publication Data

US 2014/0039287 A1 Feb. 6, 2014

Related U.S. Application Data

(63) Continuation of application No. 13/541,111, filed on Jul. 3, 2012, now Pat. No. 8,626,268, which is a continuation of application No. 10/097,096, filed on Mar. 14, 2002, now abandoned.

(60) Provisional application No. 60/275,486, filed on Mar. 14, 2001.

(51) Int. Cl.
*A61B 6/00* (2006.01)
*A61B 5/00* (2006.01)
*A61B 1/00* (2006.01)
*A61B 5/02* (2006.01)
*A61B 1/04* (2006.01)
*G06T 7/40* (2006.01)
*A61B 5/07* (2006.01)
*G06T 7/00* (2006.01)

(52) U.S. Cl.
CPC .............. *A61B 5/743* (2013.01); *A61B 5/0031* (2013.01); *A61B 5/0075* (2013.01); *A61B 5/0084* (2013.01); *A61B 1/00009* (2013.01); *G06T 2207/30028* (2013.01); *A61B 5/02042* (2013.01); *A61B 1/041* (2013.01); *G06T 7/408* (2013.01); *A61B 1/00045* (2013.01); *G06T 2207/10024* (2013.01); *G06T 2207/10068* (2013.01); *A61B 5/073* (2013.01); *G06T 7/0012* (2013.01)
USPC ........... 600/476; 600/407; 600/473; 600/101; 600/103; 600/109; 600/112; 600/160; 600/176; 600/177; 600/178; 600/179; 600/180; 348/65; 348/68

(58) Field of Classification Search
USPC .................................. 600/302, 407, 473, 476
See application file for complete search history.

(56) References Cited

U.S. PATENT DOCUMENTS

| 5,604,531 A * | 2/1997 | Iddan et al. ..................... 348/76 |
| 6,422,994 B1 * | 7/2002 | Kaneko et al. ................ 600/160 |
| 2002/0042562 A1 | 4/2002 | Meron et al. |

FOREIGN PATENT DOCUMENTS

WO       WO 00/22975 A1 *   4/2000   ............... A61B 1/04

OTHER PUBLICATIONS

Office Action issued by the United States Patent and Trademark Office for U.S. Appl. No. 13/541,111 dated Jun. 12, 2013.
Notice of Allowance issued by the United States Patent and Trademark Office for U.S. Appl. No. 13/541,111 dated Sep. 24, 2013.

* cited by examiner

*Primary Examiner* — James Kish
(74) *Attorney, Agent, or Firm* — Pearl Cohen Zedek Latzer Baratz LLP

(57) ABSTRACT

A system and method for detection of colorimetric abnormalities within a body lumen includes an image receiver for receiving images from within the body lumen. Also included are a transmitter for transmitting the images to a receiver, and a processor for generating a probability indication of presence of colorimetric abnormalities on comparison of color content of the images and at least one reference value.

14 Claims, 5 Drawing Sheets

METHOD AND SYSTEM FOR DETECTING COLORIMETRIC ABNORMALITIES IN VIVO

CROSS-REFERENCE TO RELATED APPLICATIONS

This application is a continuation application of U.S. patent application Ser. No. 13/541,111, filed on Jul. 3, 2012, which is a continuation application of U.S. patent application Ser. No. 10/097,096, filed Mar. 14, 2002, which claims priority from U.S. Provisional Patent Application No. 60/275,486, filed Mar. 14, 2001, all of which are incorporated herein by reference in their entirety.

FIELD OF THE INVENTION

The present invention relates to a method and system for detection of colorimetric abnormalities in vivo, and specifically within the gastrointestinal (GI) tract.

BACKGROUND OF THE INVENTION

Pathologies of the gastrointestinal (GI) tract may exist for a variety of reasons. Some examples of pathologies include bleeding, lesions, angiodisplasia, Crohn's disease, polyps, celiac disorders, and others. The majority of pathologies result in changes of color and/or texture of the inner surface of the GI tract.

As one example, color changes may be due to bleeding. Blood may be present within the digestive tract for a variety of pathological reasons, including ulcers, cancer, or other disease conditions. It is often difficult to detect the presence of blood within the GI tract, since bleeding can occur in difficult to reach locations. In addition, it is difficult to "see" inside the tract, especially in sections which are hard to reach such as the small intestines.

Several approaches have been used to try to detect the presence of blood within the GI tract. One approach has been the detection of blood in the feces by visual and/or chemical means. The main drawback of this approach has been that the concentration of blood in the feces is lower than the concentration of blood at the bleeding site since additional materials are accumulated along the GI passage. Therefore, the sensitivity of this approach is low. In addition, the specific bleeding site along the GI tract cannot be determined.

A second, more invasive technique, has been the use of an endoscope or enteroscope. This approach enables direct visualization of parts of the GI tract. However, most portions of the small intestine are inaccessible by this method.

Other examples of pathologies which may be detected based on the red part of the spectrum include active bleeding, blood clots, polyps, lesions, ulcerations, angiodispiasia and telangectasia. Pathologies which may be characterized by blue/violet color include arterio-venous malformation (AVM) and submucosal bleeding. AVM may also appear in red. In addition, some types of ulcers are characterized by white color.

SUMMARY OF THE INVENTION

There is provided, in accordance with one embodiment of the present invention, a method for detecting colorimetric abnormalities in a body lumen. The method includes the step of calculating a probability indication of a presence of an abnormal color within the body lumen based on comparison of spectral characteristics to at least one reference value.

There is provided, in accordance with another embodiment of the present invention, a method for calculation of a reference value for tissue. The method includes the steps of receiving at least a first image and a second image from within a body lumen, selecting blocks of pixels within the images based on colorimetric parameters, averaging the colorimetric parameters of the selected blocks of pixels of the first and second images, and filtering the colorimetric parameters, thereby obtaining a reference value for tissue.

There is provided, in accordance with another embodiment of the present invention, a swallowable capsule for detecting colorimetric abnormalities in a gastrointestinal tract. The capsule includes an image-receiver for receiving images from the gastrointestinal tract, and a processor for generating a probability indication for presence of colorimetric abnormalities by comparing color content of the images to at least one reference value.

There is provided, in accordance with another embodiment of the present invention, an apparatus for determining colorimetric abnormalities within a body lumen. The apparatus includes an image-receiver for receiving images from a body lumen, a spectral analyzer for determining color content of the images, and a processor for generating a probability indication for presence of an abnormal condition by comparing the color content to at least one reference value.

There is provided, in accordance with another embodiment of the present invention, a system for detection of blood within a body lumen. The system includes a swallowable capsule having an in-vivo imager for obtaining images from within the body lumen, a transmitter for transmitting the images to a receiver, and a processor for generating a probability indication of presence of blood based on comparison of color content of the received images and at least one reference value.

BRIEF DESCRIPTION OF THE DRAWINGS

The present invention will be understood and appreciated more fully from the following detailed description taken in conjunction with the drawings in which.

DETAILED DESCRIPTION OF THE INVENTION

The present invention relates to a method and system of detection of pathologies by spectral analysis of images captured by a moving in vivo video camera system. This analysis is based on detection of colorimetric abnormalities, or deviations from an expected spectrum. The in-vivo video camera system may be included on an endoscope, a swallowable capsule, or any other device which is introduced into the body to view the interior.

U.S. Pat. No. 5,604,531, assigned to the common assignee of the present application and incorporated herein by reference, teaches an in vivo camera system, which is carried by a swallowable capsule. The in vivo video camera system captures and transmits images of the GI tract while the capsule passes through the GI lumen, in addition to the camera system, the capsule contains an optical system for imaging an area of interest onto the camera system and a transmitter for transmitting the video output of the camera. The capsule can pass through the entire digestive tract and operate as an autonomous video endoscope. It images even the difficult to reach areas of the small intestine.

Figure 1:
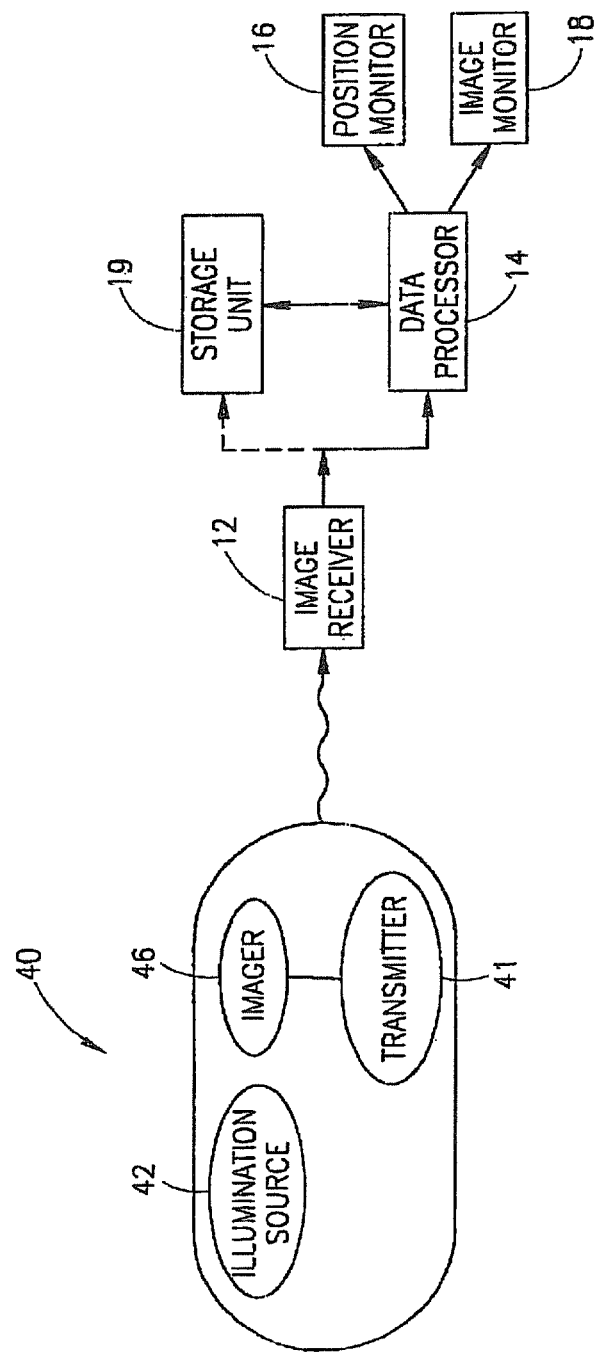
FIG. 1 is a schematic illustration of a prior art in vivo camera system.

Reference is made to FIG. 1, which shows a schematic diagram of the system, described in U.S. Pat. No. 5,604,531. The system comprises a capsule 40 having an imager 46, an illumination source 42, and a transmitter 41. Outside the patient's body are an image receiver 12 (usually an antenna array), a storage unit 19, a data processor 14, an image monitor 18, and a position monitor 16. While FIG. 1 shows separate monitors, both an image and its position can be presented on a single monitor.

Imager 46 in capsule 40 is connected to transmitter 41 also located in capsule 40. Transmitter 41 transmits images to image receiver 12, which sends the data to data processor 14 and to storage unit 19. Data processor 14 analyzes the data and is in communication with storage unit 19, transferring frame data to and from storage unit 19. Data processor 14 also provides the analyzed data to image monitor 18 and position monitor 16 where the physician views the data. The image monitor presents an image of the GI lumen and the position monitor presents the position in the GI tract at which the image was taken. Data processor 14 can be configured for real time processing or for post processing to be viewed at a later date. In addition to revealing pathological conditions of the GI tract, the system can provide information about the location of these pathologies.

In a preferred embodiment of the present invention, received images are analyzed for color content. Based on this analysis, as described hereinbelow, determination as to the presence or absence of a colorimetric abnormality may be made. A colorimetric abnormality may indicate a pathological condition, such as bleeding. Other examples of pathologies which may be detected based on the red part of the spectrum include active bleeding, blood clots, polyps, lesions, ulcerations, angiodisplasia and telangectasia. Pathologies which may be characterized by blue/violet color include arterio-venous malformation (AVM) and submucosal bleeding. AVM may also appear in red. In addition, some types of ulcers are characterized by white color. It will be apparent that the method and system described hereinbelow may be useful in detecting any colorimetric deviation from the normal color content of a body lumen, whether or not a pathological condition is present.

Figure 2:
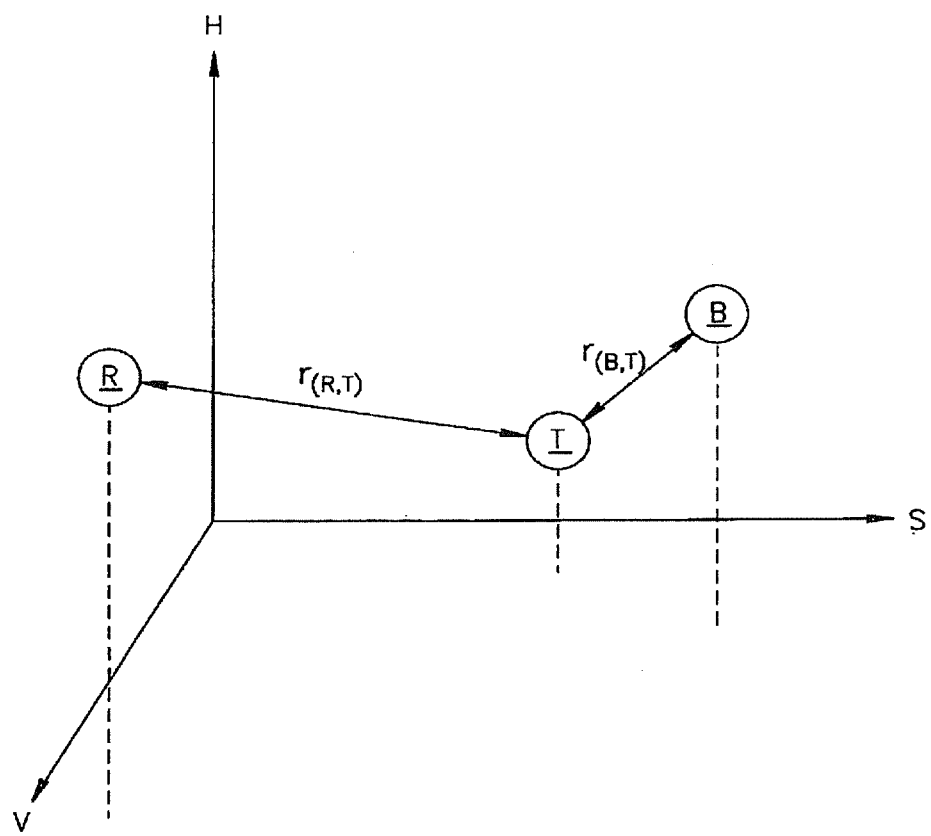
FIG. 2 is a schematic illustration of the classification of samples according to their spectral components.

Reference is now made to FIG. 2, which is a schematic illustration of the classification of samples according to their spectral components. Each test sample T is located within a coordinate system represented by the following variables: hue H, saturation S and value V. Hue H represents a number related to the dominant wavelength of the color stimulus, and varies from 0 to 1 as the color changes from red to yellow to green to cyan to blue to magenta and back to red again. Saturation S corresponds to color purity, and in the case of a pure color is equal to 100%. Value V is a measure of relative intensity of color, representing brightness of red, blue and green (RBG). A distance vector r(B,T) between test sample T and an ideal pathology sample B is calculated. Another distance vector r(R,T) between test sample T and a reference sample of healthy tissue R is calculated. The relationship of distance vector r(B,T) and distance vector r(R,T) is calculated. Each test sample T is classified based on the relationship between distance vector r(B,T) and distance vector r(R,T). Briefly, if distance vector r(B,T) is small relative to distance vector r(R,T), there is a positive indication of pathological color. In the preferred embodiment, the analysis is set up to include a higher possibility of false positives than false negatives, so as to minimize the likelihood of missing a positive diagnosis. However, other embodiments of analysis are possible as well.

Figure 3:
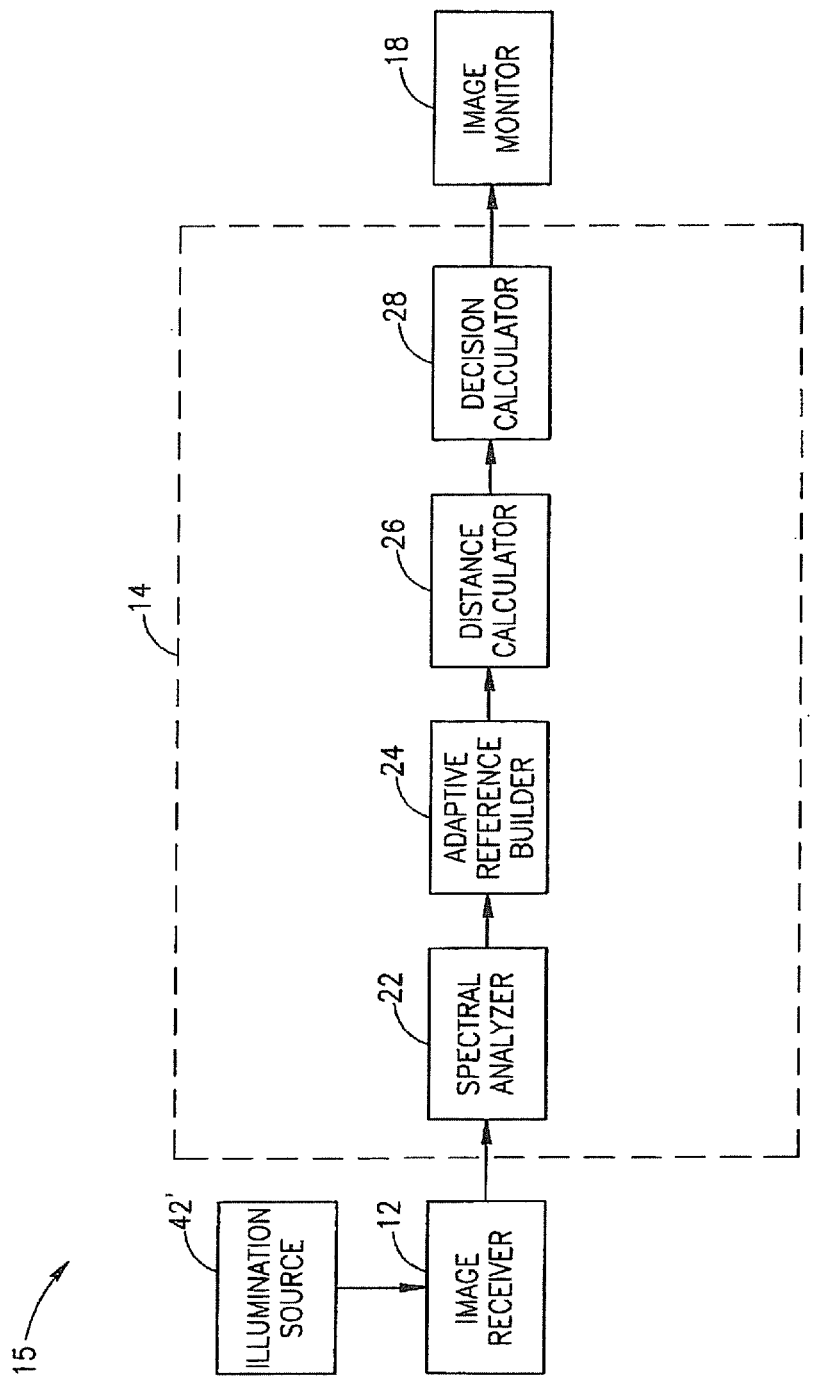
FIG. 3 is a block diagram illustration of a system according to one embodiment of the present invention.
Figure 4:
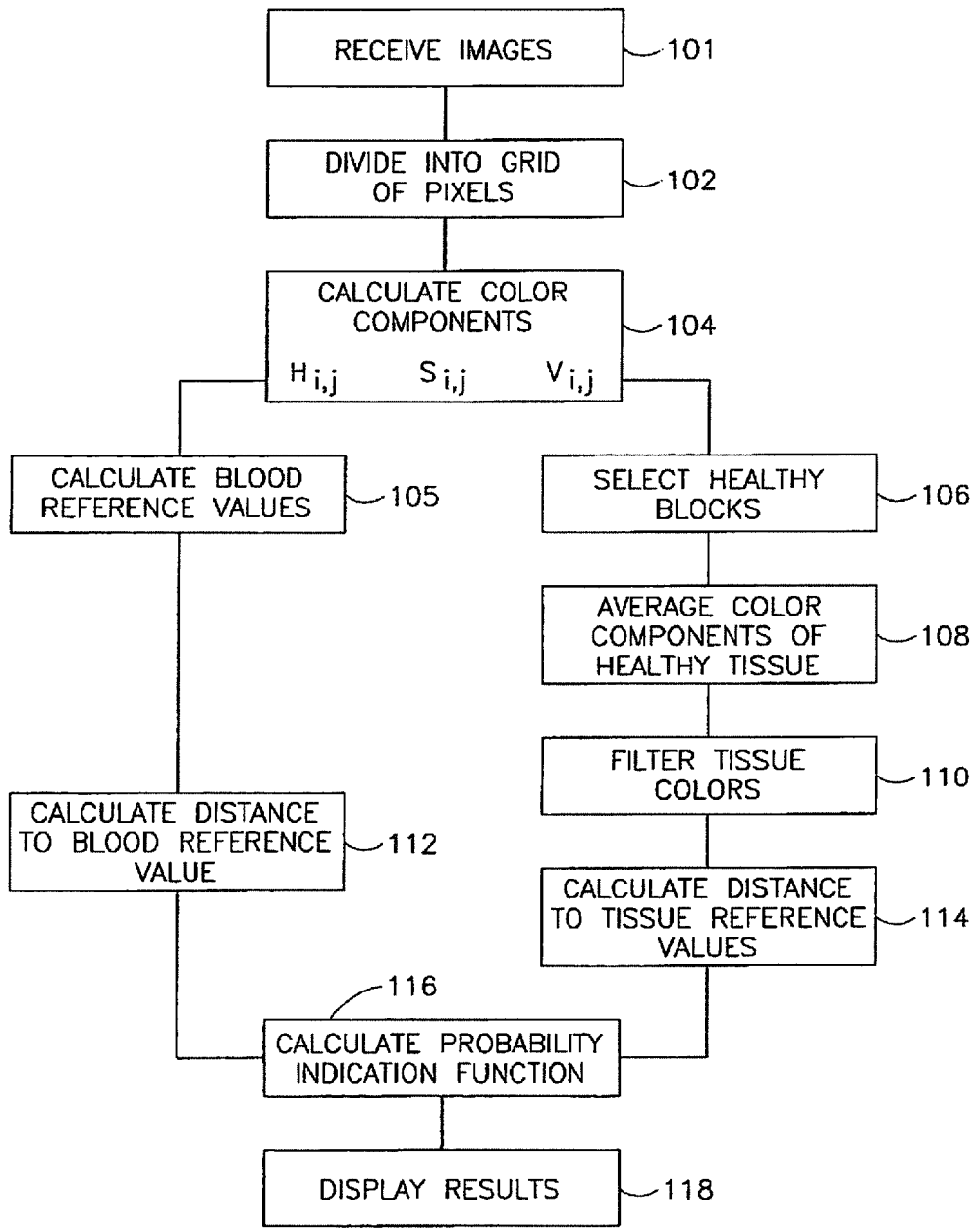
FIG. 4 is a flow chart illustration of the method used by the system shown in FIG. 3.

Reference is now made to FIGS. 3 and 4, which illustrate a system 15 and a flow chart diagram showing the steps of using system 15 for determining the blood content or any other color-distinguishable pathology within the gut. System 15 comprises illumination source 42', image receiver 12', data processor 14', and image monitor 18'. Data processor 14' comprises a spectral analyzer 22, an adaptive reference builder 24, a distance calculator 26, and a decision calculator 28. According to one embodiment of the invention, data processor 14' is a standard computer accelerator board, high performance computer, multiprocessor or any other serial or parallel high performance processing machine. Image monitor 18' may be a video display, or a graph, table or any other indicator.

Steps of FIG. 4 may be accomplished using system 15 of FIG. 3. In one embodiment, images are captured and processed within a capsule. In another embodiment, images are captured by an in-vivo system, and are transmitted to a remote location where they are processed. Image receiver 12' receives (step 101) images captured by the in-vivo camera system of FIG. 1 or any other in-vivo imager. Data processor 14' divides (step 102) the color images into a grid of pixels. As in other imaging applications, the number of pixels determines the resolution of the image. For purposes of this discussion, the images are divided into blocks (i,j) of 8×8 pixels. Since, in one embodiment, the original image is a 256×256 pixel image, the result of dividing into 8 pixels, and determining the color components is a 32×32×3 matrix of color component value blocks. Spectral analyzer 22 calculates (step 104) the color components of each block: hue $H_{i,j}$; saturation $S_{i,j}$; and brightness value $V_{i,j}$ for each image.

Spectral analyzer also calculates (steps 105 and 106-110) the color components of blocks of pathology sample B and of healthy reference tissue R. Spectral analyzer 22 calculates (step 105) the color components of blocks of pathology sample B from known images containing blood.

Figure 5:
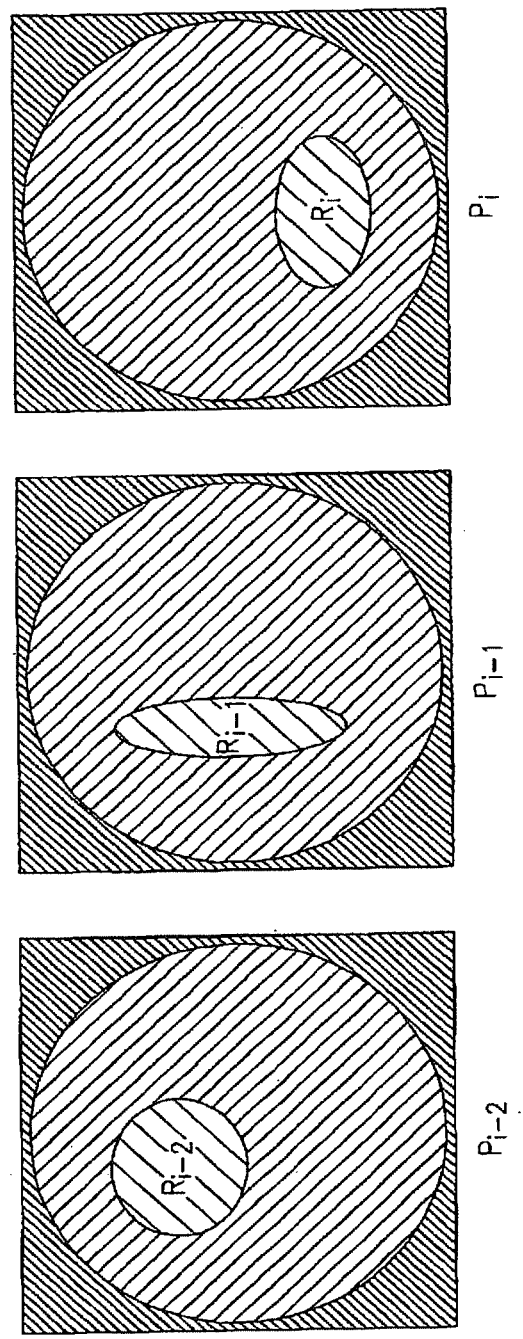
FIG. 5 is a schematic illustration of adaptive building of a reference tissue sample.

Reference is now made to FIG. 5, which is a schematic illustration of the adaptive reference building steps 106-110 of FIG. 4. Adaptive reference builder 24 calculates (steps 106-110) tissue reference color components in order to build a reference sample of healthy tissue. The adaptive approach is based on averaging healthy tissue appearing in subsequent images. Averages are used since the parameters of healthy tissue along the GI tract may change. Adaptive reference builder 24 selects (step 107) blocks based on value V (brightness) and hue H. In one embodiment, the conditions are: $0.1<V_{i,j}<0.9$ and $0<H_{i,j}<0.09$. These conditions indicate that healthy tissue is present. As shown in FIG. 5, images $P_i$, $P_{i-1}$, and $P_{i-2}$ with regions $R_i$, $R_{i-1}$, and $R_{i-2}$ of healthy tissue are obtained. Adaptive reference builder 24 averages (step 108) color components of healthy regions $R_i$, $R_{i-1}$, and $R_{i-2}$ (i.e. the selected blocks) of images $P_i$, $P_{i-1}$, and $P_{i-2}$ obtained along the GI tract. To smooth the data and eliminate sensitivity to particular images, adaptive reference builder 24 filters (step 110) the average tissue colors of the present image $P_i$ and the previous image $P_{i-1}$.

In one embodiment an Infinite Impulse Response (IIR) filter with the following iterative computation is used:

$$\text{out}(t_i)=0.08*\text{in}(t_i)+0.92*\text{out}(t_{i-1})$$

where $t_i$ represents the time index of the current frame i and $t_{i-1}$ represents the time index of the previous frame i−1.

Referring back to FIG. 4, distance calculator 26 then calculates (step 112) the Euclidian distance between each block in the matrix and blood reference value B. Blood reference value B is obtained from known images containing blood, analyzed by spectral analyzer 22 as described above. In another embodiment, a different colorimetric reference value may be used for indication of other unusual colors. The result of this calculation, for the exemplary embodiment, is a matrix of 32×32 elements $\beta_{i,j}$. This calculation is done according to the following equation:

$$\beta_{i,j} = \frac{\sqrt{(H_{i,j} - H_b)^2 + (S_{i,j} - S_b)^2 + (V_{i,j} - V_b)^2}}{\sqrt{(H_b^2 + S_b^2 + V_b^2)} * \sqrt{(H_{i,j}^2 + S_{i,j}^2 + V_{i,j}^2)}}$$

where $H_b$, $S_b$ and $V_b$ are the reference values for hue, saturation and brightness, respectively, of blood.

A similar distance calculation is calculated relative to the adaptive tissue reference color (healthy tissue) components, resulting in a 32×32 matrix $\theta_{i,j}$ as follows, $$\vartheta_{i,j} = \frac{\sqrt{(H_{i,j} - H_t)^2 + (S_{i,j} - S_t)^2 + (V_{i,j} - V_t)^2}}{\sqrt{(H_t^2 + S_t^2 + V_t^2)} * \sqrt{(H_{i,j}^2 + S_{i,j}^2 + V_{i,j}^2)}}$$

where $H_t$, $S_t$ and $V_t$ are the reference values for hue saturation and brightness, respectively, of healthy tissue.

Once the distance matrices are obtained, decision calculator 28 calculates (step 116) a probability indication function Λ according to the following equation:

$$\Lambda = \Sigma_{i,j} \left\{ (\beta_{i,j} \leq BloodThreshold) \cap \left( \frac{\vartheta_{i,j}}{\beta_{i,j}} \geq TissueRatioThreshold \right) \right\}$$

The threshold can be set to any value. In a preferred embodiment, the threshold values are as follows: BloodThreshold=0.15 and TissueRatioThreshold=4. Blood exists if Λ>0.

Finally, image monitor 18' displays (step 118) the results, either as a color video showing the presence of blood, or as a graph or table indicating the levels and/or threshold values.

Display of results may include incorporation of a position indicator, so that the end user can determine where the presence of color change is within the GI tract, or other body lumen. Thus, the physician will be able to deal with the problem area.

It will be appreciated by persons skilled in the art that the present invention is not limited to what has been particularly shown and described hereinabove. Rather the scope of the present invention is defined only by the claims that follow:

What is claimed is:

1. A method for displaying in-vivo information, the method comprising:
   receiving at a data processor data generated by a swallowable in-vivo device traversing a GI tract, the data comprising a set of in-vivo images of the GI tract;
   for each image of said set, the data processor calculating:
   (i) a first distance between a colorimetric value of the image and a first reference value, wherein the first reference value corresponds to predetermined colorimetric values obtained from in-vivo images showing blood in the GI tract, and (ii) a second distance between said colorimetric value of the image and a second reference value, wherein the second reference value corresponds to colorimetric values obtained from in-vivo images showing healthy GI tract tissue;
   the data processor further, based on the first distance and the second distance, causing to be displayed a probability indication of presence of blood corresponding to a position in the GI tract.

2. The method of claim 1, comprising: the data processor comparing the first distance to a first predetermined threshold and the data processor comparing the second distance to a second predetermined threshold.

3. The method of claim 2, comprising: the data processor calculating the probability indication of presence of blood, based on the comparison of the first distance and the comparison of the second distance.

4. The method of claim 1, comprising: the data processor dividing the image into blocks of pixels, and wherein the first distance is calculated between a colorimetric value of each block and the first reference value and the second distance is calculated between a colorimetric value of each block and the second reference value.

5. The method of claim 1, wherein the colorimetric value of the image includes hue, saturation, and brightness of pixels in the image.

6. The method of claim 1, wherein the second reference value corresponds to colorimetric values obtained from images from the set.

7. A system for displaying in vivo information, comprising:
   a data processor configured to:
      receive data collected by a swallowable in-vivo device traversing a GI tract, the data comprising a set of in-vivo images of the GI tract,
      for each image of said set, calculate: (i) a first distance between a colorimetric value of the image and a first reference value, wherein the first reference value corresponds to predetermined colorimetric values obtained from in-vivo images showing blood in the GI tract, and (ii) a second distance between said colorimetric value of the image and a second reference value, wherein the second reference value corresponds to colorimetric values obtained from in-vivo images showing healthy GI tract tissue, and
      based on the first distance and the second distance, generate probability indications of presence of blood corresponding to a position in the GI tract.

8. The system of claim 7 wherein the data processor is configured to compare the first distance to a first predetermined threshold, and to compare the second distance to a second predetermined threshold.

9. The system of claim 8, wherein the data processor is to configured to calculate, based on comparison of the first distance and the comparison of the second distance, the probability indication of presence of blood.

10. The system of claim 7, comprising a monitor to display a color video showing the presence of blood and, based on said probability indications, an indication of the location of blood in the GI tract.

11. The system of claim 7, wherein the data processor is configured to divide each image into blocks of pixels, and wherein the first distance is calculated between a colorimetric value of each block and the first reference value and the second distance is calculated between a colorimetric value of each block and the second reference value.

12. The system of claim 7, wherein the colorimetric value of the image includes hue, saturation, and brightness of pixels in the image.

13. A method for displaying in-vivo information, the method comprising:
- receiving at a data processor data generated by a swallowable in-vivo device traversing a GI tract, the data comprising a set of in-vivo images of the GI tract;
- for each image of said set, the data processor calculating: (i) a first distance between a colorimetric value of the image and a first reference value, wherein the first reference value corresponds to predetermined colorimetric values obtained from in-vivo images showing color in a red part of a color spectrum in the GI tract, and (ii) a second distance between said colorimetric value of the image and a second reference value, wherein the second reference value corresponds to colorimetric values obtained from in-vivo images showing healthy GI tract tissue;
- the data processor further, based on the first distance and the second distance, causing to be displayed probability indications of presence of colorimetric abnormality corresponding to a position in the GI tract.

14. The method of claim 13, wherein the colorimetric abnormality is selected from the group of bleeding, blood clots, polyps, lesions, ulcerations, angiodisplasia and telangiectasia.

* * * * *